US009795388B1

(12) United States Patent
Evans

(10) Patent No.: US 9,795,388 B1
(45) Date of Patent: Oct. 24, 2017

(54) SURFACE CONFIGURATION OF IMPLANTABLE DEVICES TO MODIFY BIOLOGICAL ACTIVITY AND RELATED METHOD

(76) Inventor: Avery Evans, Charlottesville, VA (US)

(*) Notice: Subject to any disclaimer, the term of this patent is extended or adjusted under 35 U.S.C. 154(b) by 237 days.

(21) Appl. No.: 13/107,810

(22) Filed: May 13, 2011

Related U.S. Application Data

(60) Provisional application No. 61/334,363, filed on May 13, 2010.

(51) Int. Cl.
*A61M 29/00* (2006.01)
*A61B 17/12* (2006.01)
*A61F 2/88* (2006.01)

(52) U.S. Cl.
CPC .... *A61B 17/12131* (2013.01); *A61B 17/1214* (2013.01); *A61B 17/1215* (2013.01); *A61B 17/12145* (2013.01); *A61B 17/12154* (2013.01); *A61F 2/88* (2013.01)

(58) Field of Classification Search
CPC .......... A61B 17/1214; A61B 17/12145; A61B 17/1215; A61B 17/12154; A61F 2/88
USPC .................. 606/200; 623/1.11, 23.64, 23.69
See application file for complete search history.

(56) References Cited

U.S. PATENT DOCUMENTS

| 6,544,275 | B1* | 4/2003 | Teoh | 606/158 |
|---|---|---|---|---|
| 2002/0120297 | A1* | 8/2002 | Shadduck | 607/2 |
| 2005/0049523 | A1* | 3/2005 | Crank | 600/585 |
| 2005/0267510 | A1* | 12/2005 | Razack | 606/200 |
| 2007/0142893 | A1* | 6/2007 | Buiser et al. | 623/1.11 |
| 2012/0209309 | A1* | 8/2012 | Chen et al. | 606/194 |

* cited by examiner

*Primary Examiner* — Diane Yabut
(74) *Attorney, Agent, or Firm* — Simana Rao, Esq.; McNeely, Hare & War LLP

(57) ABSTRACT

The invention relates to an aneurysm coil that is made up of a single wire of a noncircular cross-sectional shape. The wire is coiled in a helical configuration to have an outer surface and an inner surface. The outer surface of the wire does not have a round outer surface. The aneurysm coil of the present invention is designed to encourage cellular adhesion and tissue growth along the coil surface by employing a wire having a substantially non-circular cross sectional area, such as a T shape, a triangle, square, rectangle, oval, pentagon, hexagon, septagon, octagon, star, rhombus, as well as a variety of non-geometric shapes. The use of a wire having such a cross sectional shape promotes endothelial cells to adhere and grow within the gaps created by the juxtaposition of the wire forming a coil, thus anchoring the coil to its intended location, promoting thrombosis, endothelial growth across the opening of the aneurysm, and eventual healing of the aneurysm.

21 Claims, 14 Drawing Sheets

SURFACE CONFIGURATION OF IMPLANTABLE DEVICES TO MODIFY BIOLOGICAL ACTIVITY AND RELATED METHOD

CROSS-REFERENCE TO RELATED APPLICATIONS

The present application relates to, and claims the priority to U.S. Provisional Patent Application Ser. No. 61/334,363 filed May 13, 2010, which is entitled "Surface Configuration of Implantable Devices to Modify Biological Activity and Related Method." The contents of the priority application are incorporated herein in their entirety by reference.

TECHNICAL FIELD

The field of the invention generally relates to aneurysm coils and their use for the treatment of aneurysms and other comparable conditions.

BACKGROUND

Since the early 1990's, aneurysm coils have been made of smooth, platinum wire. More recently, aneurysm coils have become available that are coated with a hydrogel material or have a PGLA suture within the coil, both of these alterations designed to help aneurysms heal. The surfaces of these coils, however, remain smooth and otherwise unmodified.

An aneurysm can be described as a bulging of a vessel wall generally caused by blood pressure acting on a weakened portion of the vessel wall. When the wall of a vessel has a weakness, the blood pressure can dilate or expand the region of the vessel at the point of weakness to form a "sac", also called a "berry" or "saccular aneurysm," shown as element 10 in FIG. 1. The pressure of an aneurysm against surrounding tissues can cause pain and tissue damage. The blood in the vicinity of the aneurysm can become turbulent, leading to the formation of blood clots, which may be carried to various body organs where they may cause various complications, including cerebrovascular incidents, myocardial infarctions and pulmonary embolisms. Should an aneurysm rupture and begin to leak blood (causing a subarachnoid hemorrhage), the condition can become life threatening within minutes.

There are various methods currently available in the art to treat aneurysms. Coil embolization is one such method which is commonly used to treat aneurysms and in many cases is considered safer for the patient than open craniotomy. In current techniques, aneurysm coils take the form of spiral-wound wires having a circular cross-section that can assume a more complex overall three dimensional shape after insertion into the aneurysm. By using a material which is highly flexible and relatively small in diameter, the coil can be installed in a catheter or micro-catheter in a relatively linear configuration and assume a more complex shape after being pushed from the distal end of the catheter using a pusher. The vascular embolization procedure typically requires the surgeon to advance a micro-catheter to a location within the aneurysm or proximal to the opening of the aneurysm. Thereafter, a biologically-compatible coil may be pushed through the catheter such that the coil is "packed" within the aneurysm such that blood flow is partially or completely blocked from flow into the aneurysm. The presence of the coil inside the aneurysm is meant to encourage clot and scar formation inside the aneurysm, and eventually growth of the lining of the blood vessel (the endothelium) across the opening of the aneurysm which protects the aneurysm from rupturing.

A problem in the field of endovascular therapy for aneurysms is the incidence of aneurysm recurrence and re-growth. Typically, aneurysm coils may fill less that fifty percent of the total volume of the aneurysm. Although this amount of filling is usually adequate to promote a decrease in blood flow initially, with time, pressure and the pulsatile flow of blood often results in the device becoming repositioned or compacted within the aneurysm, thereby forming cavities or areas that can result in recurrent aneurysm formation. The ability for blood to flow into the aneurysm in this way despite the presence of a coil can lead to recanalization of the aneurysm with significant consequences such as rupture or tearing of the wall of the aneurysm. It is thus an advantage of one or more embodiments of the current invention to reduce the likelihood of such repositioning and/or compaction of the coil by providing a coil which encourages cellular adhesion and tissue growth on the surface of the coil, thus improving the likelihood of anchoring the coil within the aneurysm space, promoting complete filling of the aneurysm with fibrous tissue and leading to growth of endothelial cells across the opening of the aneurysm sealing off the aneurysm from the vascular system and thereby protecting the aneurysm from bleeding.

As noted above, prior art coils are known. For example, Ferrera et al. (US 2003/0199887) and Jones et al. (US 2003/0004531) disclose a porous or textural embolization devices, and Lorenzo et al. (US 2006/0200190) discloses either one or two wires which are helically wound to form a coil. Attempts also have been made to coat coils with a growth-promoting composition. For example, Greene et al (U.S. Pat. No. 6,299,619) discloses a device which can carry hydrogel, drugs or other bioactive materials to stabilize or reinforce the aneurysm. Another treatment disclosed in Evans et al. (U.S. Pat. No. 6,335,384) comprises catheter delivery of platinum microcoils into the aneurysm cavity in conjunction with an embolizing composition comprising a biocompatible polymer and solvent. The deposited coils or other non-particulate agents are said to act as a lattice about which a polymer precipitate grows thereby embolizing the blood vessel. The wires used in forming these prior art coils are typically of the standard round shape having a circular cross section, with a particular diameter specified, or with respect to Lorenzo et al., utilize a helically twisted or wound wire. As is illustrated in the scanning electron micrographs of FIGS. 4-6, the extent of cellular growth along the surface of prior art coils, such as those having a circular cross section, is not optimized for endothelial growth.

Aneurysm coils should not only occupy as much of the volume of the aneurysm as possible and encourage the growth of fibrous tissue and endothelium as described above, they should also have other desirable properties including softness and predictable folding characteristics. Aneurysms are by their very nature thin walled structures that are prone to rupture. As a result, aneurysm coils should be soft, pliant and fold in ways that do not put undue pressure on the walls of the aneurysm. For instance, if an aneurysm coil is too stiff, then when it emerges from the catheter it may be prone to pierce the wall of the aneurysm and cause a hemorrhage in the brain. If the coil folds in a way that creates a sharp or acute angle, this acute angle may likewise be prone to put undesired focal pressure on the wall of the aneurysm, at the risk of rupturing it and causing hemorrhage. Thus, any design of an aneurysm coil must engender both softness and predictable bendability with non-sharp or non-acute angles to avoid dangerous pressure on the walls of the aneurysm.

The delivery mechanics of many of these prior art aneurysm treatment methods can therefore be difficult and complicated due, in part, to i) the problems associated with deploying such coils and ii) the inherent nature of introducing foreign substances in vivo. As such, there is a need in the art for a simple and inexpensive coil design with predictable packing characteristics and is also effective at promoting cellular adhesion and tissue growth along the coil. Such a coil design is believed to result in anchoring the coil within the aneurysm to effectively eliminate blood flow therein, and providing a substrate for endothelium to grow across the opening of the aneurysm sealing it off from the flow of blood in the vessel.

Accordingly, one or more embodiments of the present invention may utilize an aneurysm coil comprising a single primary wire having a non-circular cross-sectional shape which may provide enhanced cellular adhesion and tissue growth along the coil surface when compared to coils employing wire having a circular cross-sectional area or coils employing two or more wires. Further, the single wire of non-circular cross section when formed into a coil may not only provide improved cellular adhesion, but also constitute a soft, non traumatic intra-aneurysmal device having the desirable properties noted above with more predictable bending and folding characteristics thereby improving the safety of using the device and placing it into the aneurysm.

The following patents, applications and publications as listed below and throughout this document are hereby incorporated by reference in their entirety herein.

1. U.S. Patent Application Publication No. US 2003/0004531, A1, Jones, et al., "Occluding Vasculature of a Patient Using Embolic Coil with Improved Platelet Adhesion", Jan. 2, 2003.

2. U.S. Patent Application Publication No. US 2004/0117004 A1, Osborne, et al., "Stent and Method of Forming a Stent with Integral Barbs", Jun. 17, 2004.

3. U.S. Patent Application Publication No. US 2009/0297582 A1, Meyer, et al., "Vascular Occlusion Devices and Methods", Dec. 3, 2009.

4. U.S. Patent Application Publication No. US 2009/0069904 A1, Picha, G., "Biomaterial Including Micropores", Mar. 12, 2009.

5. International Patent Application Publication No. WO 95/22305, Curtis, et al., "Wound Healing Material", Aug. 24, 1995.

6. Curtis, et al., "Topographical Control of Cells", Biomaterials 1997, Vol. 18, No. 24, 1573-1583.

7. Eliaz, et al., "The Effect of Surface Treatment on the Surface Texture and Contact Angle of Electrochemically Deposited Hydroxyapatite Coating and on its Interaction with Bone-Forming Cells", Acta Biomater, 2009.

8. Matsuzaka, et al., "The Attachment and Growth Behavior of Osteoblast-like Cells on Microtextured Surfaces", Biomaterials 24, 2003, 2711-2719.

SUMMARY

In one general aspect there is provided an aneurysm coil that is made up of a single wire of a noncircular cross-sectional shape. The wire is coiled in a helical configuration to have an outer surface and an inner surface. The outer surface of the wire does not have a round outer surface.

Embodiments of the aneurysm coil may include one or more of the following features. For example, the aneurysm coil may include one or more gaps formed between adjacent sections of the wire along a length of the helical coil. The aneurysm coil may be free of a second wire. The wire may have a cross-sectional shape of one or more of a triangle, square, rectangle, oval, pentagon, hexagon, septagon, octagon, star or rhombus that vary or are constant along the length of the wire.

At least a portion of the outer surface of the wire may be a textured surface. At least a portion of the textured surface of the wire may be flat.

At least a portion of the wire may be coated with one or both of a bioabsorbable material and a nonbioabsorbable material. The coil may form a hollow inner region and the inner region may include one or more of a bioabsorbable material, a nonbioabsorbable material and a hydrogel or mixtures thereof.

At least a portion of the outer surface of the wire may be flat.

The wire may be made of one or more of a metal, plastic material, and/or hydrogel material.

In another general aspect there is provided a method of treating an arterial aneurysm. The method includes:

providing an aneurysm coil comprising a single wire of a noncircular cross-sectional shape, wherein the wire is coiled in a helical configuration to have an outer surface and an inner surface, wherein the outer surface of the wire does not have a round outer surface;

delivering the aneurysm coil to the arterial aneurysm; and releasing the aneurysm coil into the aneurysm coil, wherein the shape of the wire provides a surface of endothelial cell deposition and growth.

Embodiments of the method may include one or more of the following features. For example, the wire may be coiled to form a gap between adjacent coils of wire. The aneurysm coil may be free of a second wire. The wire may have a cross-sectional shape comprising one or more of a triangle, square, rectangle, oval, pentagon, hexagon, septagon, octagon, star or rhombus and the shape is constant or varying along the length of the wire.

At least a portion of the outer surface of the wire may be a textured surface. At least a portion of the textured surface of the wire may be flat.

The wire may be made of one or more of a metal, plastic material, and/or hydrogel material metal.

The arterial aneurysm to which the coil is delivered may be a cerebral aneurysm or an aortic aneurysm.

In another general aspect there is provided a process for forming an aneurysm coil. The process uses additive processing to deposit the material to form the coil. Embodiments of the process may include one or more of the following features or those listed above. For example, the additive processing method may be one or more of laser deposition, electron beam melting, aerosol jetting, inkjet deposition, semi-solid free form fabrication.

In another embodiment, the aneurysm coil is formed by a single wire having a noncircular cross-sectional shape wound into an elongated helical coil defining an unoccupied inner region extending through the helical coil. The outer surface of the wire does not have a round outer surface. One or more gaps may be formed between adjacent sections of the wire along a length of the helical coil. The wire may have a cross-sectional shape comprising one or more of a triangle, square, rectangle, oval, pentagon, hexagon, septagon, octagon, star, rhombus, spiral or any other non round geometric or nongeometric shape. At least a portion of the surface of the wire may be textured. The textured wire portion may include an edge portion and/or a flat surface portion. At least a portion of the wire may be covered with a bioabsorbable material or a non-bioabsorbable material.

At least a portion of the inner region of the coil may be occupied by a bioabsorbable material, a nonbioabsorbable or hydrogel material provided in a non-wire form.

In another aspect the invention relates to an aneurysm coil and a method for treating an aneurysm using the aneurysm coil. The coil has a single wire wound into an elongated helical coil having one or more gaps between adjacent sections of the wire along a length of the coil. The coil has an outer surface adapted to promote cellular growth thereon and a hollow interior permitting the coil to bend for deposition within an aneurysm. The shape of the wire provides a surface of endothelial cell deposition and growth. The aneurysm coil is free of a second wire.

The wire may have a cross-section which varies along the length of the wire. The cross-section of the wire may vary in terms of diameter, and/or shape, either geometric or non-geometric.

The aneurysm coil may be covered at least in part with a bioabsorbable material, a non bioabsorbable material, or hydrogel. The coil defines an inner region occupied at least in part by a bioabsobable material, a non-bioabsobable material, or hydrogel material.

The cross-sections of the wire may be different in terms of composition of materials. The coil may be covered at least in part with a bioabsorbable material or a non bioabsorbable material. The inner region may be occupied at least in part by a bioabsobable material or at least in part by a non-bioabsobable material or at least in part by hydrogel material.

DETAILED DESCRIPTION

Figure 1:
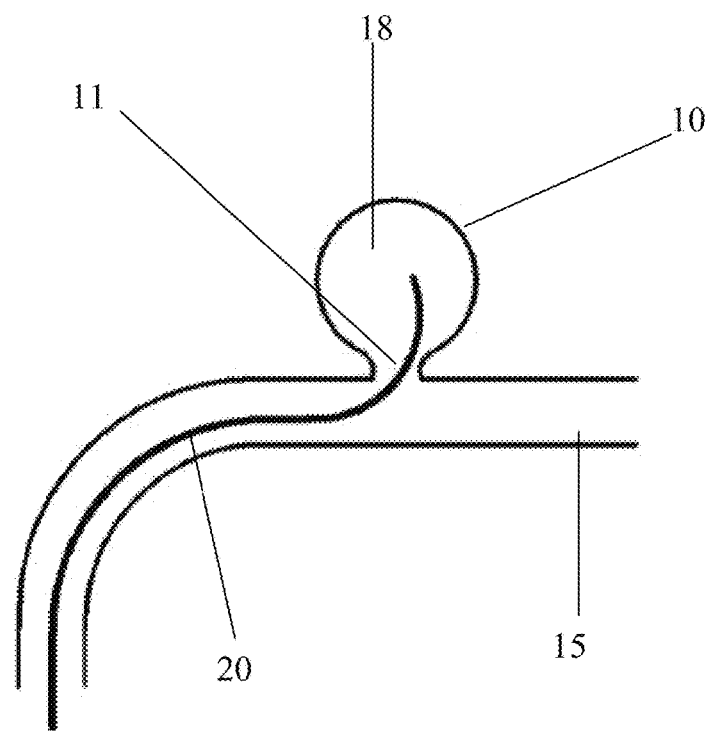
FIG. 1 illustrates an aneurysm formed on a blood vessel of a patient with a catheter inserted therein in accordance with one embodiment of the present invention.

An aspect of an embodiment of the present invention provides the capability of providing endothelial cells that can be stimulated to anchor and grow on aneurysm coils that have surface modification. An aspect of an embodiment of the present invention provides an efficient and effective way to modify the surface of the aneurysm coil to enhance its healing properties without significantly changing its mechanical properties for aneurysm embolization. An aspect of an embodiment of the present invention provides the application of an implantable device into the human body (or animal) that results in a response from the tissue involved. For instance, biological tissues such as endothelial cells react in various ways to the surface characteristics of aneurysm coils deposited with in the aneurysm sac to promote thrombosis and eventual healing of the aneurysm.

An aspect of an embodiment of the present invention provides the capability for endothelial cells to react to gaps in metallic surfaces of the aneurysm coils, in such a way that gaps on the surface the metal of a certain width and depth promote significantly faster and a more robust epithelial deposition than smooth surfaces. In another embodiment, gaps may be created by the juxtaposition of the coils themselves the surface of which may be flat, rounded, or angulated so that a regular series of gaps is created between the aneurysm coils.

An aspect of an embodiment of the present invention provides a surface of an implantable device configured or adapted to create a regular or irregular series of clefts that create an environment that either encourages or retards the growth of endothelium and fibrous tissue.

An aspect of an embodiment of the present invention provides a surface of implantable devices such as for aneurysm coils and stents that is configured or adapted with a regular series of gaps. These gaps may range in widths from approximately 10 nm to 10 mm. The gaps may range in depth from approximately 10 nm to 10 mm. The gaps can be spaced approximately 10 nm or up to 10 mm apart. The gaps may be straight and parallel in configuration, curvilinear and parallel in configuration or non parallel and either straight or curvilinear in configuration.

The gaps may be created on the surface of devices made of metal, plastic, ceramic or hydrogel material.

In an embodiment, gaps may be created by the juxtaposition of the elements of the devices themselves so that a regular series of gaps is created between the aneurysm elements of the device, the surface of which may be flat, rounded, or angulated. For example, the elements of the device that are usually made up of a single smooth, rounded wire could be composed of multiple smaller wires that are braided in a way that leaves gaps between the smaller wires, or the elements of the device that are normally composed of a smoothly rounded wire could be made of a wire that is a shape other than round, such as square, rectangular, triangular or flat so that when these elements are composed into a device, gaps are created in and on the surface of the device. More specifically the element that comprises the primary wind of the coil being made of metal, plastic, ceramic or a composite material may be of a shape other than round such as oval, square, rectangular, or any other none round shape. Likewise, the primary wind need not be regular along its length so that it could vary from one shape to another lengthwise. Either of these elements when constructed into a secondary wind would create a texture on the surface of the secondary wind that could act to alter the biological activity of the coil.

It is worth noting that the medical device market is a multibillion dollar industry. For instance, in the aneurysm coil market, coils that are reported to have biological activity can sell for as much as twice the price of standard bare metal coils.

The aneurysm coil of the present invention is designed to encourage cellular adhesion and tissue growth along the coil surface by employing a wire having a substantially non-circular cross section, such as a T shape, a triangle, square, rectangle, oval, pentagon, hexagon, septagon, octagon, star, rhombus, as well as a variety of non-geometric and/or irregular shapes. The wire may have one of the above-mentioned non-circular cross-sectional shapes along its length and may, in some embodiments, alternate from one cross-sectional shape to another, or may employ a variety of cross-sectional shapes with no pattern associated therewith. Embodiments of the present invention may allow for improved cellular growth on the surface of the aneurysm coil after insertion into an aneurysm sac, thus anchoring the coil to its intended location, promoting thrombosis, endothelial growth across the opening of the aneurysm, and/or eventual healing of the aneurysm. The aneurysm coil of the present invention may also stimulate natural cellular growth and proliferation within vascular aneurysms and across the openings of aneurysms, thus allowing for the stabilization and sealing off of aneurysms in a biologically sound, effective and lasting manner.

It is the discovery of the inventor that endothelial cells have a strong propensity to bridge gaps on the surface of materials with which they come into contact. Embodiments of the present invention may provide the capability for endothelial cells to adhere and grow within gaps (i.e., small open spaces defined by the side wall surface(s) of the wire making up the coil) which are created by the juxtaposition of sequential, adjacent coils of the wire. The gaps preferably have a width and depth which promotes more rapid and robust endothelial deposition. The wire surfaces may be convex, concave, flat, rounded (e.g., oval), or angulated such that it forms a regular or irregular series of gaps along the surface of the coil and also between the aneurysm coils (if more than one is used), each of which may have an identical length or dissimilar lengths. Gaps may also be created on the surface of the wire itself through the application of texture or holes within the wire. In general, however, the wire does not have a circular cross-section.

The use of the wire having a non-circular cross sectional area may enhance cellular adhesion and proliferation on the surface of the coil as well as within and across the gaps provided between each adjacent wind of the coil. The shape of the aneurysm coil of one or more embodiments of the present invention may thus be such that endothelial cells and fibroblasts have an affinity for the coil and thus results in robust cellular growth on the surface of the coil such that the coil may eventually become a biointegrated part of the healed aneurysm. The coil may also be more biocompatible and elicit less adverse biological response on delivery or after occlusion and healing of the aneurysm. This is in contrast to the results illustrated in FIGS. 4-6 of less than robust cellular growth on the coil surface.

Embodiments of the present invention may also enhance healing properties without significantly changing the coil's mechanical properties for aneurysm embolization and deployment. The coil of the present invention preferably employs a single primary wire or an alternating primary single wire to form its coil structure, the wire(s) having a cross sectional area which is non-circular. The absence of a second wire allows the coil to bend predictably, therefore allowing the surgeon to effectively control the coil and have a lesser tendency to scratch or tear at the surface of the vessel wall during deployment.

Employing wire having a non-circular cross sectional area such as a triangle, square, rectangle, oval, pentagon, hexagon, septagon, octagon, star, rhombus, or a variety of non-geometric shapes, may result in increased cell adhesion and tissue growth at the aneurysm-coil interface, thus leading to improved tissue healing within the aneurysm and reduced risk of aneurysm recurrence or re-growth.

FIG. 1 shows an aneurysm 10 having a neck portion 11 in communication with a blood vessel 15 and a dome portion defining an aneurismal cavity 18. Those skilled in the art will appreciate that FIG. 1 illustrates an exemplary vascular aneurysm and is not intended to limit the scope or intent of the present invention or its field of use. Embodiments of the present invention may be used to fill, treat or otherwise impart therapeutic effects to vascular anomalies formed throughout the body. For example, the aneurysm may be a cerebral aneurysm in the brain and can be of a variety of sizes from very small to large. If such an aneurysm cannot be surgically corrected, a catheter-based delivery device may be necessary to treat the aneurysm.

Figure 2:
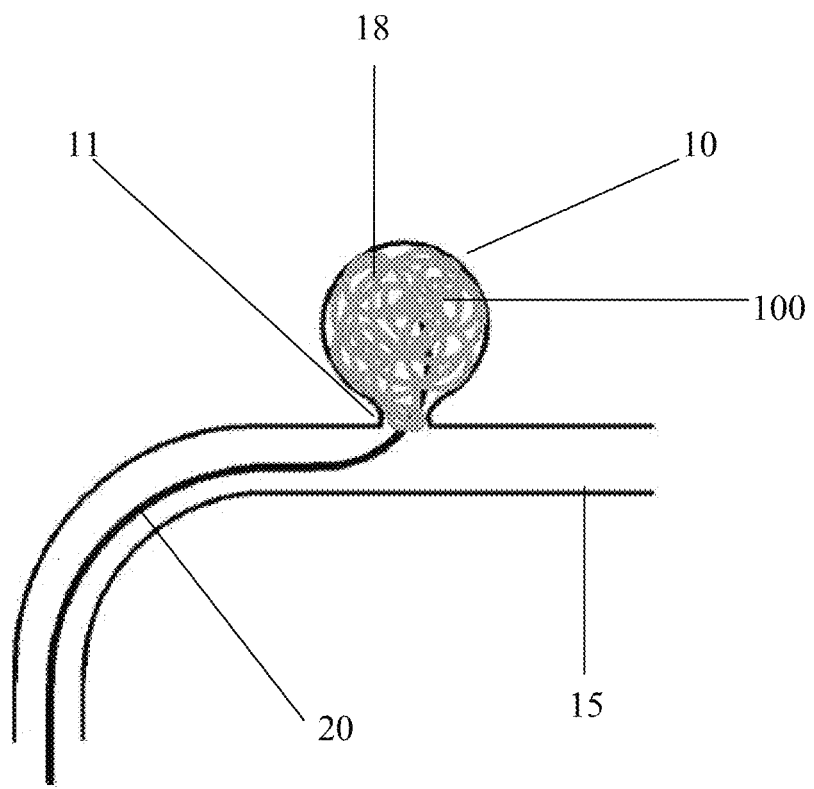
FIG. 2 illustrates the aneurysm of FIG. 1 with the coil of one embodiment of the present invention being deployed within the aneurysm.

As shown in FIG. 2, in accordance with an embodiment of the present invention, an aneurysm coil employing a wire or wires having a substantially non-circular cross sectional area is used to embolize an aneurysm 10. FIG. 2 shows aneurysm 10 having a neck portion or opening 11 in communication with a blood vessel 15. A delivery device 20 is inserted into the vasculature, e.g., through the femoral artery, and advanced into the blood vessel 15 and used to deposit the aneurysm coil 100 into aneurysm cavity 18. The aneurysm coil 100 may be inserted into aneurysm 10 in a variety of ways, including, without limitation, conventional surgical techniques and minimally invasive surgical techniques utilizing catheters of various sizes, including micro-catheters and other instruments generally known in the art.

Figure 3:
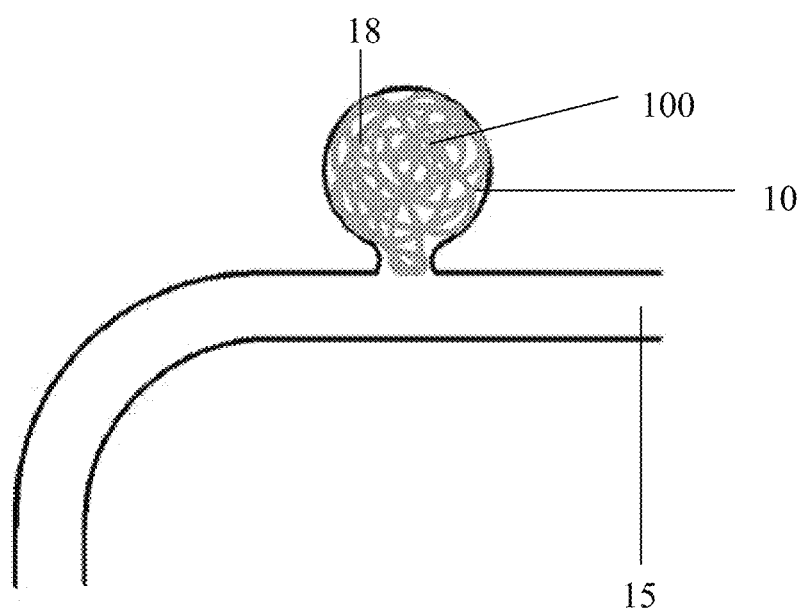
FIG. 3 illustrates an aneurysm formed on a blood vessel of a patient with the coil of one embodiment of the present invention being in the deployed state within the aneurysm and the catheter taken out of the patient.

In practice, a first incision is made to access a blood vessel. A guidewire may be inserted into the catheter and advanced through the blood vessel to the site of the aneurysm. Commonly, the guidewire will enter the circulatory system through the femoral artery, the femoral vein, the jugular vein, the carotid artery, or a similar blood vessel. The delivery device 20 is next advanced over the guidewire such that the distal end is near or within the aneurysm. The guidewire is next removed and the surgeon positions the aneurysm coil 100 on or within a delivery device 20 such as a catheter or micro-catheter. The aneurysm coil is then controllably advanced through the delivery device 20 and into the aneurysm 10. Multiple aneurysm coils may be delivered into the aneurysm cavity until the aneurysm cavity 18 is filled or partially filled with aneurysm coils 100. As illustrated in FIG. 3, when the aneurysm cavity 18 is sufficiently filled by the aneurysm coils 100, the delivery device 20 is removed from the aneurysm and vasculature. Typically, visualization methods such as fluoroscopy, ultrasound visualization, x-ray, or echogenic visualization are utilized to precisely position the delivery device 20 near the aneurysm neck 11 or within the aneurysm 10. Most typically, fluoroscopy will be used to visualize the delivery device.

Figure 4:
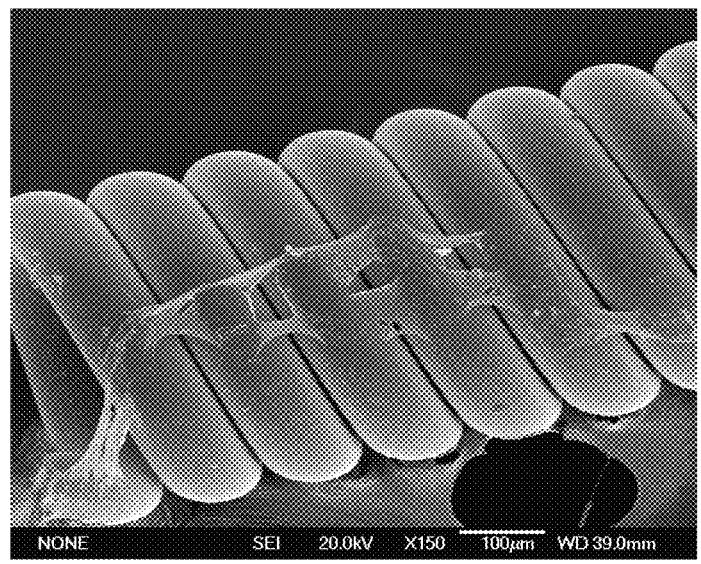
FIGS. 4-5 are scanning electron microscope (SEM) images of a prior art coil employing a wire having a circular cross sectional area, having an enlargement at 150×.
Figure 5:
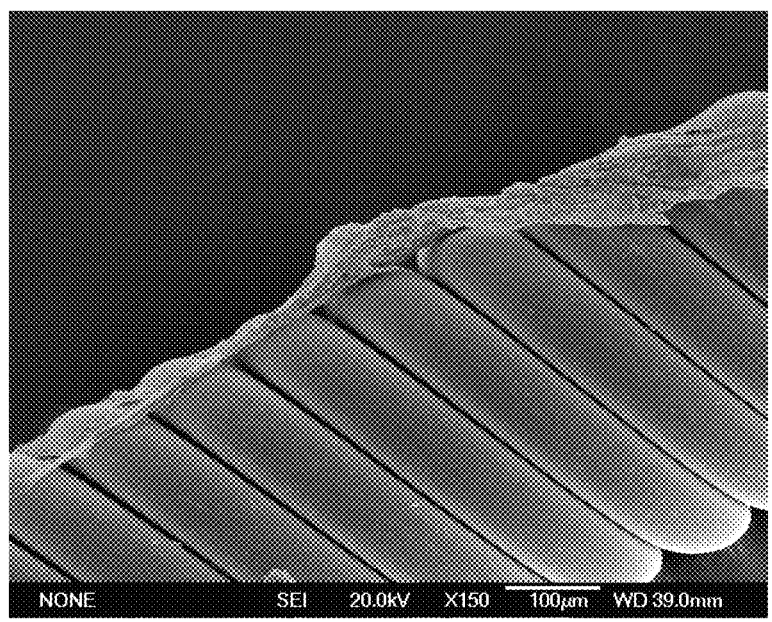
Figure 6:
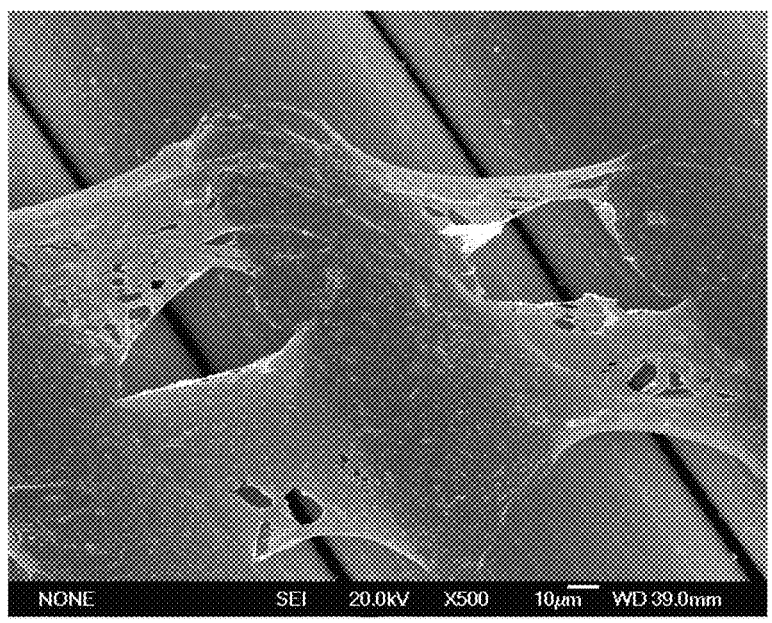
FIG. 6 is an SEM image of a prior art coil employing a wire having a circular cross sectional area, having an enlargement at 500×.

SEM micrographs of prior art coils employing circular cross sectional wires are provided in FIGS. 4-6. Testing was conducted by subjecting 5 mm sections of coil to a standard medium for endothelial growth, such as MCDB 131 (by Invitrogen™) reduced serum-supplemented medium for culture of human microvascular endothelial cells. An amount of human brain endothelial cells is added to the medium. The coil segments are incubated in the media for approximately 30 minutes and thereafter transferred into a 0.1% gelatin dish (for example, G1393 Gelatin solution by Sigma-Aldrich®) and incubated for an additional 12-24 hours. The coils are then washed with phosphate buffer saline solution and fixed with 4% PFA before being prepared according to commonly known methods for SEM imaging. The SEM images demonstrate that the endothelial cells have a propensity to bridge the gaps that are present in the coils. For instance, the lower left aspect of the coil of FIG. 4 depicts an endothelial cell that has preferentially spanned a gap from one surface to another, the gap measuring approximately 50-100 µm. Note in FIGS. 4 and 5 that all visualized cells align themselves to span the gaps that are present in the coil. This recent observation is in contrast to the current thought in the medical device industry that endothelial cells have a propensity to grow within the crevices between each coil windings.

In comparison to the coils having a circular cross section, a superior platelet/endothelial cell adhesion is expected using the present inventive coil constructed from wire having a non-circular cross sectional area. In particular, it is expected that the coil of the present invention has an increased platelet/endothelial cell deposition of at least 5% or more when compared to circular cross sectional wire. In another embodiment, the coil of the present invention provides an increased platelet/endothelial cell deposition of at least 10% or more, 20% or more, or 30% or more when compared to circular cross sectional wire. As a result, the inventive coil provides superior platelet, fibroblast and endothelial cell adhesion which promotes clotting and tissue growth within the aneurysm. In addition to providing a surface that promotes cellular adhesion and growth, the ridges and gaps that are embodied in the present invention also provide areas that will be sheltered from the flow of blood, creating zones where blood flows slowly or even not at all, zones and locations where blood cells and other cells such as endothelial cells can pool and collect, promoting clotting, thrombosis and cellular growth and deposition.

Endothelial cells may also attach preferentially to textured surfaces rather than smooth surfaces. FIG. 4 depicts a prior art coil which in its lower left hand aspect, demonstrates endothelial cell growth to the relatively rough textured cut surface of the coil. Thus, it is one aspect of the invention that the inventive coil 100 employ texture which further enhances the preferential adherence of endothelial cells to the non-circular coil surface or wire.

Figure 7A:
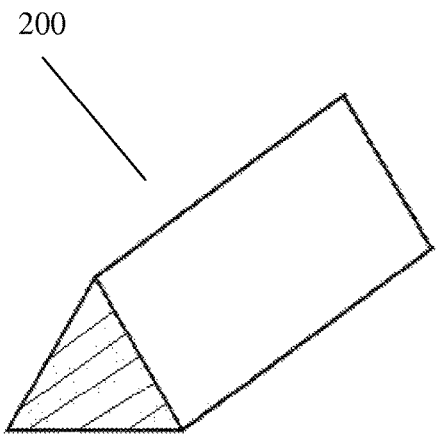
FIGS. 7A-7B depict a section of one embodiment of the wire of the present invention having a substantially triangular cross section.
Figure 7B:
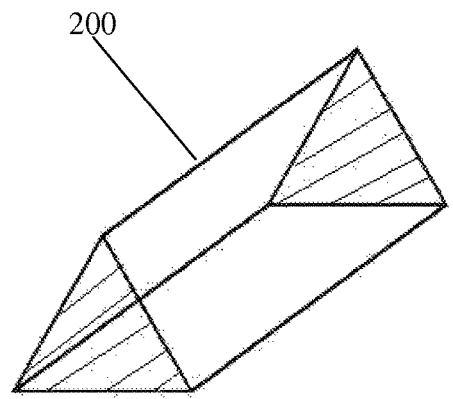
Figure 8A:
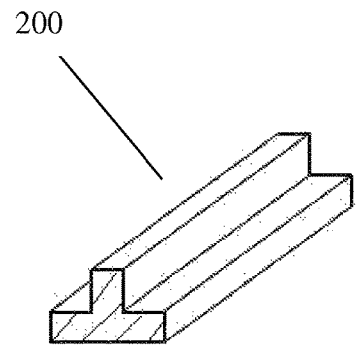
FIGS. 8A-8B depict a section of one embodiment of the wire of the present invention having a substantially T-shaped cross section.
Figure 8B:
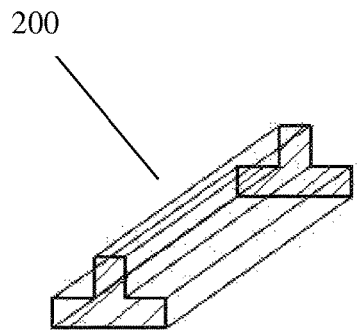

FIGS. 7A and 7B depict a section of the wire 200 which forms the aneurysm coil 100. FIGS. 7A and 7B depict one embodiment of the wire 200 having a cross sectional shape which is triangular shaped. The wire may be solid (as shown in FIG. 7A) or hollow (as shown in FIG. 7B). FIGS. 8A and 8B similarly depict one embodiment of the wire 200 having a T-like cross sectional shape. The wire may be solid (as shown in FIG. 8A) or hollow (as shown in FIG. 8B).

Figure 9A:
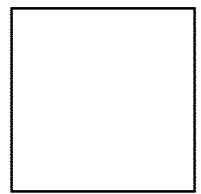
FIGS. 9A-9O depict a variety of possible cross sectional shapes of wire to be used according to the present invention.
Figure 9B:
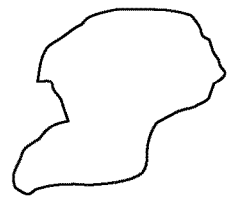
Figure 9C:
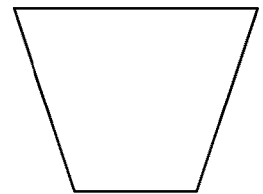
Figure 9D:
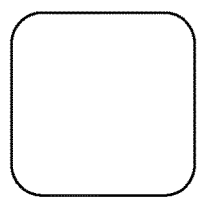
Figure 9E:
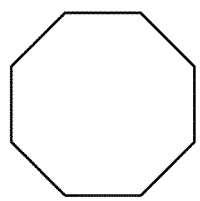
Figure 9F:
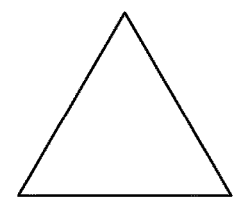
Figure 9G:
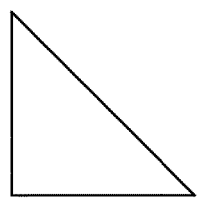
Figure 9H:
Figure 9I:
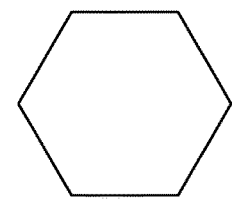
Figure 9J:
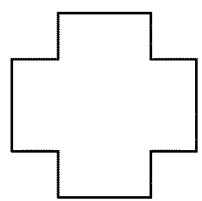
Figure 9K:
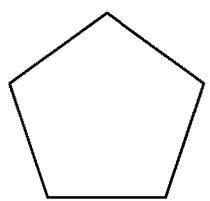
Figure 9L:
Figure 9M:
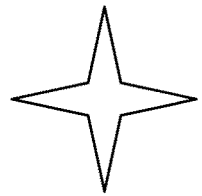
Figure 9N:
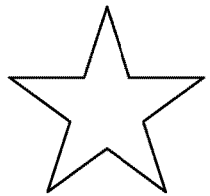
Figure 9O:
Figure 10:
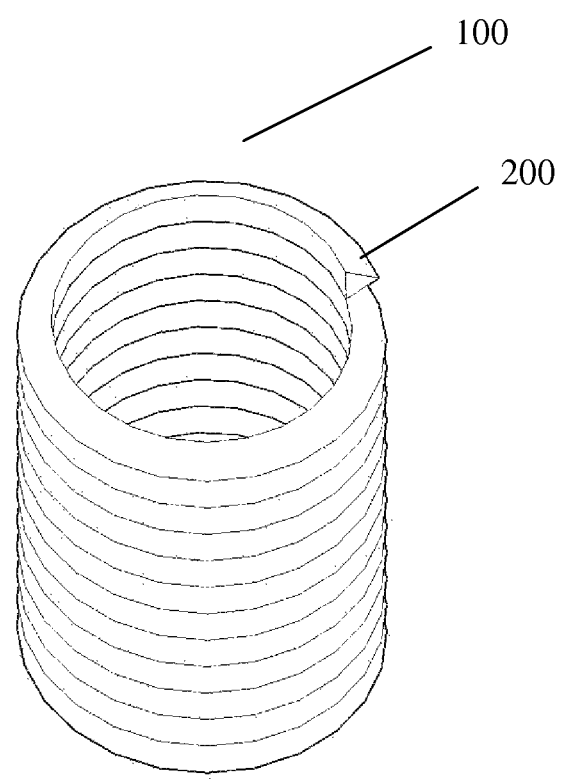
FIG. 10 depicts a perspective view of the coil in accordance with one embodiment of the present invention wherein the wire has a triangular cross sectional shape.

FIGS. 9A to 9O depict a cross sectional view of a plurality of embodiments of wire 200. The wire 200 may have a substantially non-circular cross sectional shape, such as a T shape, a triangle, square, rectangle, oval, pentagon, hexagon, septagon, octagon, star, rhombus, as well as a variety of non-geometric shapes. The wire 200 may be shaped into more than one of the above-mentioned non-circular shapes along its length which may either alternate from one shape to another, or may employ a variety of shapes with no pattern associated therewith. For example, the wire may have a triangular cross sectional area (or any other non-circular shape) through its entire length, as is shown in FIG. 10 as coil 100. Alternatively, the wire 200 may have a triangular cross sectional shape (or any other non round shape) and a square cross sectional shape (or any other non round shape) which alternates along its length. Employing wire having a non-circular cross sectional area as described herein results in increased cellular adhesion and tissue growth at the aneurysm-coil interface, thus leading to improved tissue healing within the aneurysm and reduced risk of aneurysm recurrence or re-growth.

In one embodiment, the wire 200 may have a cross sectional shape which can be of variable dimensions (such as width, height, etc.) along its length. For example, if the wire 200 has a triangular cross sectional shape, the size of the triangle may be altered along the length of the wire, the variable size alternating either with or without a pattern.

In another embodiment, one or more surfaces of the wire 200 could be textured. For example, one surface of a wire having a triangular cross section may be textured and another side left smooth. One surface of a wire having a T shaped cross section may be textured and an adjacent surface left smooth. These surfaces could be alternated in a regular or irregular pattern.

In another embodiment, the edge of the non round wire 200 where two sides meet (e.g. the apex of a triangle as in FIG. 15) could be shaped, polished, grooved or otherwise modified to enhance attachment and stimulate the growth of endothelial cells.

In another embodiment, two or more primary wires could be juxtapositioned side-by-side to create the coil structure. The primary wires making up the coil structure may provide additional surface area for cellular adhesion and bridging of cells between regular and irregular surfaces of the coil. One or more of the primary wires may have a non-circular cross sectional shape, such as a T shape, a triangle, square, rectangle, oval, pentagon, hexagon, septagon, octagon, star, rhombus, as well as a variety of non-geometric shapes. Employing two or more primary wires as part of the structure making up the coil may enhance the healing characteristics of the coil without sacrificing the mechanical characteristics of the coil. Employing two or more primary wires as part of the structure making up the coil may actually enhance the mechanical properties of the coil and one who is skilled in the art of making such coils could use this design to produce coils that are softer, less stiff and more safely and efficiently packed into an aneurysm than coils that are presently constructed of round wire or with twisted wire.

Wire 200 may be made from a variety of biologically-compatible materials, including, for example, platinum, gold, tantalum, titanium, stainless steel, tungsten, and alloys thereof, Nitinol, shape memory alloys, polyurethane, polyvinyl alcohol, polyester, polytetrafluoroethylene, silicone, acrylic, or other suitable material. Wire 200 may also be made of one material and then coated with another. For example, wire 200 may be made of any metal then coated with any other metal, for example, by electroplating. For instance, gold has a long history of being a biologically active metal so that electroplating the wire 200 of any shape with gold may prove efficacious in stimulating endothelial attachment and growth.

Wire 200 may incorporate materials that are imaged or detected using fluoroscopy, x-ray, magnetic resonance, or ultrasound. Such materials may be, for example, radioopaque materials or echogenic materials, thereby enabling the radiologist or cardiologist to precisely position the aneurysm coil 100 within the blood vessel. For example, wire 200 may employ platinum markers or structural elements such as filaments formed of polymeric fiber, carbon fiber, glass fiber, synthetic suture, a single platinum wire, nitinol wires or ribbons, other metallic fiber, a twist or braid of platinum wire and polymeric fiber or filament, or twisted or braided double platinum wires or other materials or combinations thereof.

Wire 200 may also be formed of a composition incorporating a bioabsorbable polymer, such as PCL/PGA (polycaprolactone/polyglycolide), or may be coated with the bioabsorbable polymer on its surface. In one embodiment, the wire 200 is formed of a hydrogel, such as those formed from cross-linked polymers such as polyvinyl pyrrolidone, polyethylene oxide, and polyesters. In another embodiment, the wire 200 is formed of a hydrogel core which is wrapped with a wire having a substantially non-circular cross sectional shape. In yet another embodiment, two or more inventive wires 200 having a non-circular cross sectional shape are braided together and thereafter formed into a helical coil 100.

The wire 200 may be chemically doped or impregnated with at least one drug, bio-active compound, or growth-promoting material to further encourage tissue growth or impart other therapeutic benefits to the tissue located near the aneurysm coil 100. For example, the present invention may incorporate various bio-active agents, proteins, peptides, marking agents, vascular endothelial growth factors (VEGF), basic fibroblast growth factors (bFGF), transforming growth factors-β (TGF-β) Hyaluronan derivatives [2,2], paracyclophanes, agenine-glycerine-aspartic acid (RGD), platelet derived growth factor (PDGF), thrombospondin 1 (TSP1), alginate, collagen, glycoprotein, glycosaminoglycan, endotehlial cells, tissue submucosa cells, tissue mucosa cells, and intestinal submucosa cells (SIS).

Use of the aneurysm coil 100 for which fibroblasts and other cells have an affinity enables the coil to eventually become a biointegrated part of the healed aneurysm. The coil 100 is biocompatible and elicits no adverse biological response on delivery or after occlusion and the healing of the aneurysm. Elastin, fibrin, collagen or other suitable clot-inducing material can also be coated onto the wire 200 to provide additional clot formation.

The wire 200 may be formed according to methods generally known to those of skill in the art, which include but is not limited to extrusion through a heated die, injection molding, co-injection molding, film blowing, compression molding, thermoforming, continuous rolling process and additive manufacturing techniques. The extrusion through a die can be achieved through a single step or by multiple steps at different temperatures and times and can be optionally followed by calendering or stretching steps. In one embodiment, wire 200 is formed from additive manufacturing processes including but not limited to laser deposition, electron beam melting, aerosol jetting, inkjet deposition, semi-solid free form fabrication, and other techniques. These additive techniques may allow the manufacture of embodiments of different shapes of wire 200 and coil 100, including geometric, non geometric and even amorphous, that might not be possible to manufacture with standard molding, extruding, continuous rolling or reductive processes.

The wire 200 may additionally be textured with one or more surface irregularities such as, for example, a groove, bump, barb, matrice, fenestration, notched, or tooth. Texturing or printing onto the wire substrate may be performed using techniques including but not limited to laser printing, ink-jet printing, hot foil/hot stamp marking, emboss or indent marking, etc.

The present aneurysm coil invention can be incorporated into the Gugliemi Detachable Coil System (GDC® coils) whereby a positively charged coil attracts negatively charged blood elements such as white and red blood cells, platelets, fibrinogen, and other clotting factors, thus inducing intra-aneurismal thrombosis.

Figure 11:
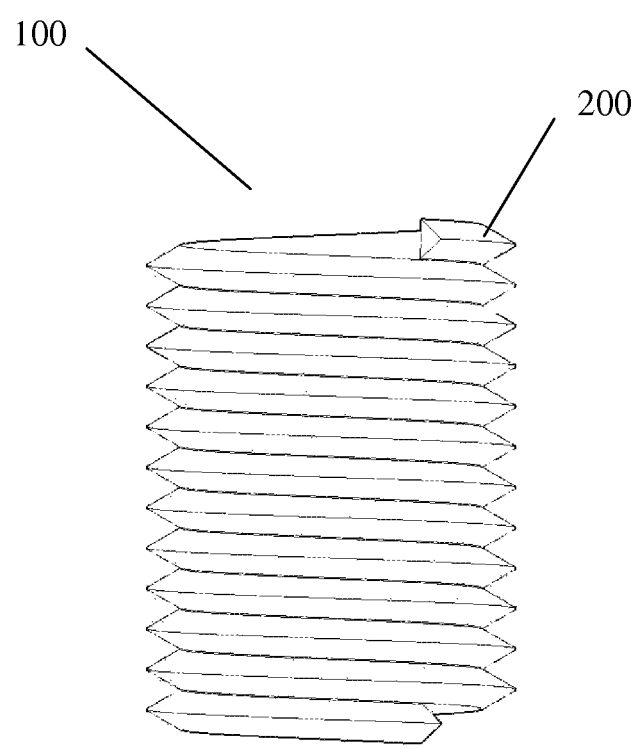
FIG. 11 depicts a side view of the coil in accordance with one embodiment of the present invention wherein the wire has a triangular cross sectional shape.
Figure 12:
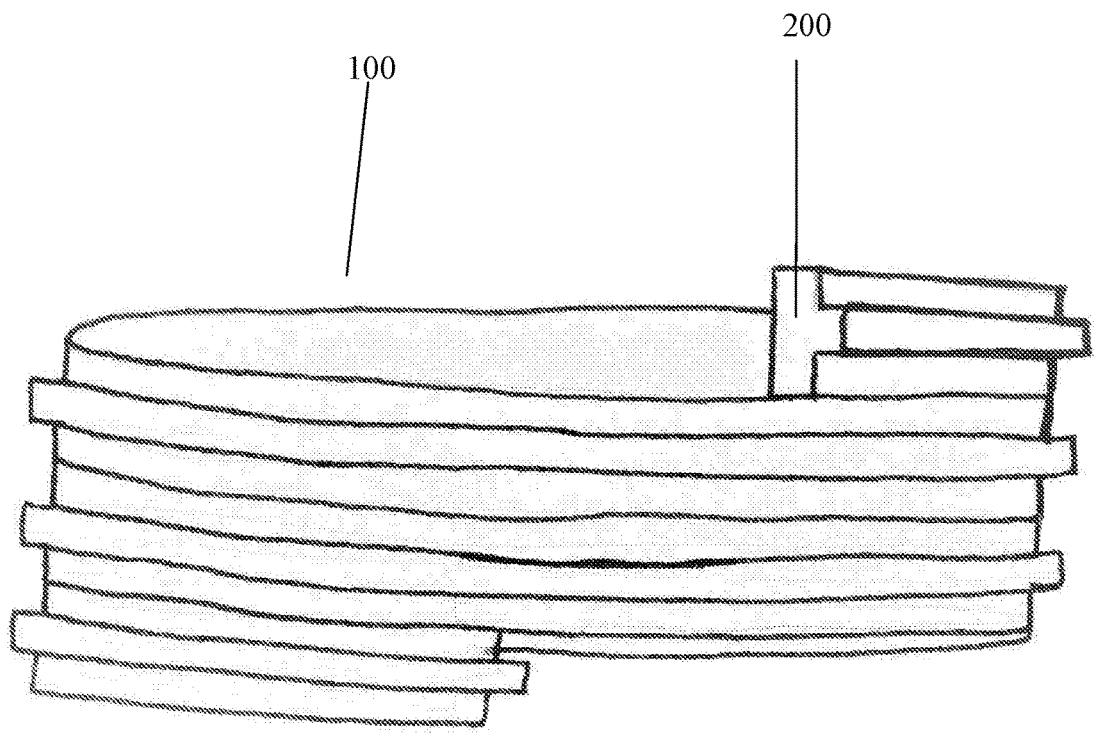
FIG. 12 depicts a side view of one embodiment of the present invention wherein the wire has a T shaped cross section.
Figure 13:
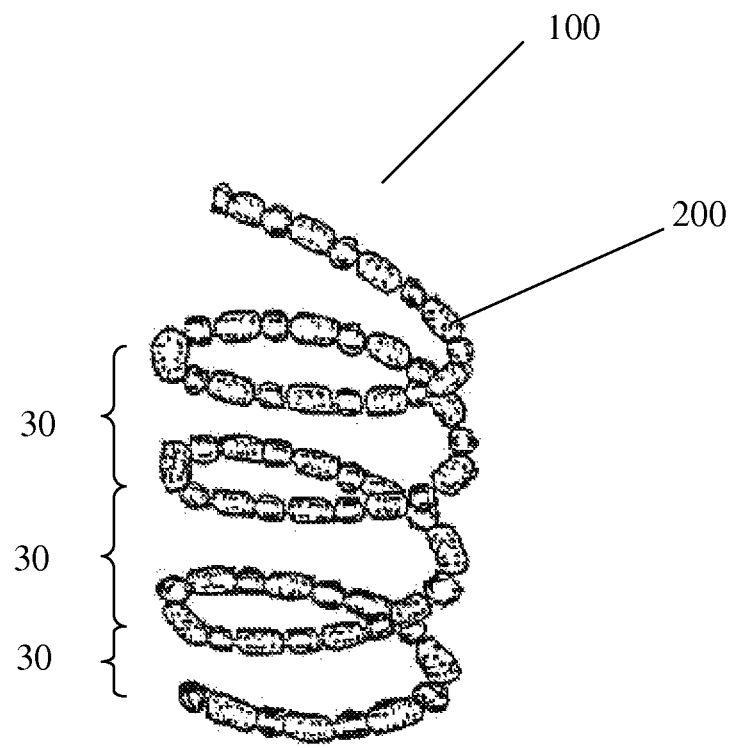
FIG. 13 depicts one embodiment of the present invention having numerous substantially non-geometric shapes having surface texturing used to form the coil.

As shown in FIGS. 10-12, the aneurysm coil 100 may be formed by winding the wire 200 having a non-circular cross sectional area into a tightly packed configuration. The wire 200 may also be wound in a loosely packed helical configuration, as is shown in FIG. 13. FIGS. 10-11 depict the inventive coil employing wire having a substantially triangular cross sectional shape. FIG. 12 depicts the inventive coil employing wire having a substantially T-shape. When the aneurysm coil 100 is in a substantially helical configuration as shown in FIGS. 10-13, the outside diameter of the coil is within a range of about 0.01 mm to 5 mm, including coils of dimensions of 0.1 mm, 0.3 mm, 0.5 mm, 0.7 mm, 1 mm, etc. as are known in the art. The aneurysm coil 100 can have a length of from about 0.5 cm to 10 cm to about 20 cm to about 30 cm in increments of single cm lengths to about 200 cm.

When the wire 200 is of a substantially triangular cross section, the length of each side may be from about 10 μm to about 150 μm up to 1 mm or more. The triangular cross section may have a height of from about 8 μm to about 140 μm to 1 mm or more.

When the wire 200 is of a substantially T-shaped cross section, the length of surface "A" (see FIG. 14) may be from about 5 μm to about 130 μm or more and the length of surface "B" may be from about 2 μm to about 90 μm or more. The T-shaped cross section may have a height of from about 15 μm to about 200 μm.

As shown in FIG. 13, gaps 30 may exist between each wind of wire. These gaps may have a length as small as about 5 nanometers and as large as about 3 mm. The gaps 30 may be of different or alternating lengths along the coil 100. The wire having a non-circular cross sectional area allows for varying surfaces to be present within the coil and between the gaps 30, such as convex, concave, flat, and curved surfaces, which amplifies endothelial, fibroblast and platelet adhesion thereon. FIGS. 10 and 11 illustrate a tightly packed aneurysm coil having a substantially small gap length between each winding of wire.

The length of the wire 200 is formed into a coil by winding the wire around a mandrel by bending the wire to form a three-dimensional shape. This three-dimensional shape may be a helix, but wire 200 may also be formed into a coil having rectangular loops rather than cylindrical loops, or other shapes such as a triangle, star, and the like.

Figure 14:
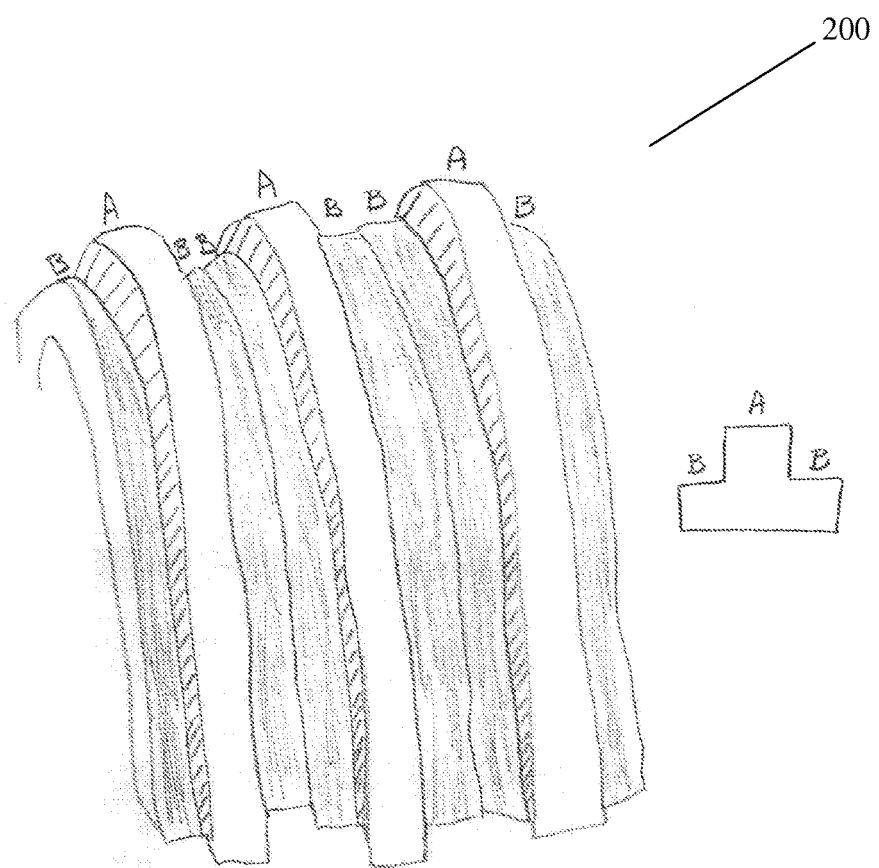
FIG. 14 depicts a surface rendering of a coil wherein the wire has a cross section that is T shaped.
Figure 15:
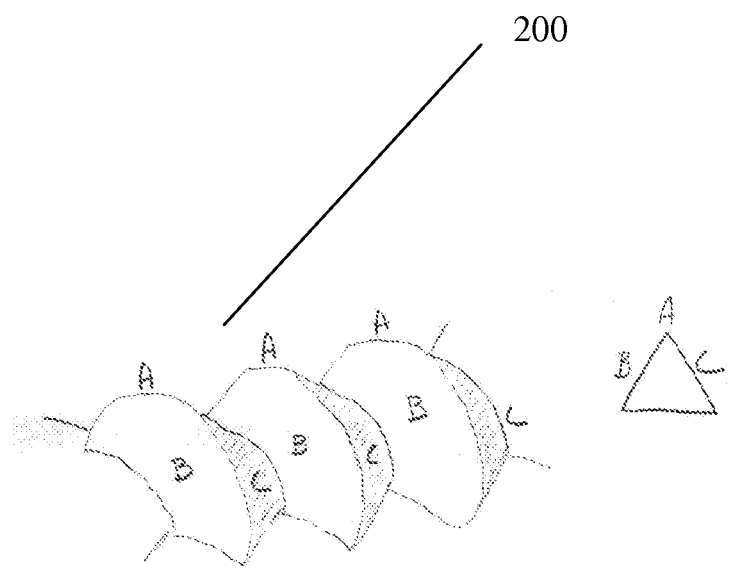
FIG. 15 depicts a surface rendering of a coil wherein the wire has a cross section that is triangular in shape and have shading on one or more surfaces. Surfaces "B" and "C" represent two adjacent sides of the triangle which meet at edge "A." Side C and edge A are textured.

The wire of the present invention has been developed due to the inventor's discovery of the strong propensity of endothelial to grow in a fashion which bridges gaps between various surfaces present in an aneurysm coil. The use of unique cross sectional shapes of wire 200 as well as an optimum gap length thus promote endothelial cells to adhere and grow across or within the gaps created by the juxtaposition of the various wires employed in the present invention. As shown in FIGS. 14 and 15, unique surfaces are formed when a wire is employed having a non-circular cross sectional shape. FIG. 14 illustrates one embodiment of the invention where "B" surfaces and "A" surfaces are created by the use of a wire having a T-shaped cross section. The use of the T-shaped cross sectional wire allows for gaps not only between each wind of wire, but also between each "A" surface, providing a regular series of gaps at an optimal length of between about 5 nanometers to about 3 mm on which endothelial growth can occur. Similarly, FIG. 15 illustrates yet another embodiment where "A", "B", and "C" surfaces are created by the use of a wire having a triangular cross section. Endothelial cell growth may bridge various gaps employed in this embodiment, including the gap between each "A" surface, the gaps between the "A" and "B" surfaces, the "A" and "C" surfaces and the "B" and "C" surfaces. Such gaps are present at an optimal length for cell growth and bridging, between about 5 nm to about 3 mm. In this way, the particular design features employed in the present invention allow for cellular growth on the surface of the inventive aneurysm coil, thus anchoring the coil to its intended location, promoting thrombosis, endothelial growth across the opening of the aneurysm, and eventual healing of the aneurysm.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Similarly, the shaped wire forming the coil may be coated with a resorbable coating that coats any sharp edges that could be deletirious during delivery but slowly dissolves while a tissue coating is formed on the surface to prevent the sharp edges from damaging the aneurysm. Such materials suitable for the coating have been listed herein but also can include any of the coatings used in the coating and pharmaceutical industry. Accordingly, it is not intended that the invention be limited, except as by the appended claims.

What is claimed is:

1. An aneurysm coil comprising a single wire having a cross-sectional shape that is substantially T-shaped along a length of at least two winds of the wire, the coil having a distal end to be advanced into the body and a proximal end, wherein the wire is coiled in a helical configuration such that the coil defines an inner surface and an outer surface, the wire having at least three substantially straight sides, wherein a first side of the wire faces the inner surface of the coil such that adjacent sections of the wire facing the inner surface form a continuous plane along the inner surface and the remaining two or more sides of the wire form at least one cleft and/or peak on the outer surface of the wire, the coil having a first point located at an outer surface of the distal end of the coil and a second point located on the outer surface of the coil proximal to the distal end of the coil, wherein the coil is configured to bend or fold to form a three dimensional substantially non-linear shape within an aneurysm to fill or pack the aneurysm such that the outer surface of the coil at the first point overlaps with the outer surface of the coil at the second point, wherein the proximal end of the coil is detachably removable from a delivery device such that the coil permanently remains inside the aneurysm and at least one cleft is formed by the two adjacent winds of wire which comprises a substrate for cell growth inside the aneurysm.

2. The aneurysm coil of claim 1, wherein one or more gaps are formed between adjacent sections of the wire along a length of the helical coil.

3. The aneurysm coil of claim 1, wherein the aneurysm coil is free of a second wire.

4. The aneurysm coil of claim 1, wherein a portion of the wire has a crossectional shape comprising one or more of a triangle, pentagon, hexagon, septagon, octagon, rhombus or non-geometric shape that varies or is constant along the length of the wire.

5. The aneurysm coil of claim 1, wherein at least a portion of the outer surface of the wire is a textured surface.

6. The aneurysm coil of claim 5, wherein at least a portion of the textured surface of the wire is flat.

7. The aneurysm coil of claim 1, wherein at least a portion of the wire is coated with one or both of a bioabsorbable material and a nonbioabsorbable material.

8. The aneurysm coil of claim 1, wherein the coil forms a hollow inner region and the inner region comprises one or more of a bioabsorbable material, a nonbioabsorbable material and a hydrogel.

9. The aneurysm coil of claim 1, wherein at least a portion of the outer surface of the wire is flat.

10. The aneurysm coil of claim 1, wherein the wire is made of one or more of a metal, plastic material, and/or hydrogel material.

11. A method of treating an arterial aneurysm, the method comprising: providing an aneurysm coil comprising a single wire having a cross-sectional shape that is substantially T-shaped along a length of at least two winds of the wire, wherein the wire is coiled in a helical configuration such that the coil defines an inner surface and an outer surface, the wire having at least three substantially straight sides, wherein a first side of the wire faces the inner surface of the coil such that adjacent sections of the wire facing the inner surface form a continuous plane along the inner surface and the remaining two or more sides of the wire form at least one cleft and/or peak on the outer surface of the wire;

delivering the aneurysm coil to the arterial aneurysm;
packing or filling the arterial aneurysm; and
releasing the aneurysm coil into the arterial aneurysm such that the coil permanently remains inside the aneurysm and at least one cleft is formed by the two adjacent winds of wire which comprises a substrate for cell growth inside the aneurysm.

12. The method of claim 11, wherein the wire is coiled to form a gap between adjacent coils of wire.

13. The method of claim 11, wherein the aneurysm coil is free of a second wire.

14. The method of claim 11, wherein a portion of the wire has a cross-sectional shape comprising one or more of a triangle, pentagon, hexagon, septagon, octagon, rhombus or a non-geometric shape that varies or is constant along the length of the wire.

15. The method of claim 11, wherein at least a portion of the outer surface of the wire is a textured surface.

16. The method of claim 15, wherein at least a portion of the textured surface of the wire is flat.

17. The method of claim 11, wherein the wire is made of one or more of a metal, plastic material, and/or hydrogel material.

18. The method of claim 11, wherein the arterial aneurysm comprises a cerebral aneurysm or an aortic aneurysm.

19. A process for forming the aneurysm coil of claim 1, the process comprising additive processing to deposit the material to form the coil.

20. The process of forming the aneurysm coil of claim 19, the additive processing method comprising one or more of laser deposition, electron beam melting, aerosol jetting, inkjet deposition, semi-solid free form fabrication.

21. An aneurysm coil comprising a single wire having a cross-sectional shape that is substantially T-shaped along a length of at least two winds of the wire the coil having a distal end to be advanced into the body and a proximal end, wherein the wire is coiled in a helical configuration such that the coil defines an inner surface and an outer surface, the wire having at least three discrete sides, wherein a first side of the wire faces the inner surface of the coil such that adjacent sections of the wire facing the inner surface form a continuous plane along the inner surface and the remaining two or more sides of the wire form a regular or irregular series of clefts and/or peaks on the outer surface of the wire
the coil having a first point located at an outer surface the distal end of the coil and a second point located at an outer surface of the coil proximal to the distal end of the coil, wherein the coil is configured to bend or fold to form a three dimensional substantially non-linear shape within an aneurysm to fill or pack the aneurysm such that the outer surface of the coil at the first point overlaps with the outer surface of the coil at the second point, wherein the proximal end of the coil is detachably removable from a delivery device such that the coil permanently remains inside the aneurysm and at least one cleft is formed by the two adjacent winds of wire which comprises a substrate for cell growth inside the aneurysm.

\* \* \* \* \*